United States Patent [19]

Lee et al.

[11] Patent Number: 4,488,549

[45] Date of Patent: Dec. 18, 1984

[54] PRESSURIZATION OF CEMENT IN BONES

[75] Inventors: Alan J. C. Lee; Robin S. M. Ling, both of Exeter, England

[73] Assignee: University of Exeter, Devon, England

[21] Appl. No.: 408,815

[22] Filed: Aug. 17, 1982

[51] Int. Cl.³ .......................... A61F 1/00; A61B 17/36
[52] U.S. Cl. .............................. 128/303 R; 128/92 C; 3/1; 3/1.9
[58] Field of Search ............. 128/92 C, 92 CA, 92 R, 128/92 G, 303 R; 3/1, 1.9, 1.91

[56] References Cited

U.S. PATENT DOCUMENTS

| | | | |
|---|---|---|---|
| 4,274,163 | 6/1981 | Malcom et al. | 3/1.91 |
| 4,338,925 | 7/1982 | Miller | 128/92 E |
| 4,399,814 | 8/1983 | Pratt, Jr. et al. | 128/92 C |

*Primary Examiner*—Richard J. Apley
*Assistant Examiner*—David J. Isabella
*Attorney, Agent, or Firm*—Larson and Taylor

[57] ABSTRACT

A seal member for fitting over and sealing the opening of a cavity in a bone to allow pressurization of cement in the cavity has an aperture for sealingly receiving a cement delivery nozzle. The seal member may be a balloon seal, which may be inflatable and expandable, or a solid body of conformable material. In use, the seal member is urged against the opening, e.g. by force applied by the barrel of a cement delivery gun on an abutment means having an apertured pressure piece shaped to urge the seal member against the mouth of the opening.

12 Claims, 11 Drawing Figures

4,488,549

PRESSURIZATION OF CEMENT IN BONES

BACKGROUND OF THE INVENTION

This invention relates to surgery in which an implant is fixed in a bone by the use of bone cement, e.g. polymethylmethacrylate bone cement.

It has been well established by laboratory experiments and clinical experience that the fixation of implants such as the components of replacement joint protheses by selfcuring polymethylmethacrylate bone cement is enhanced if the bone cement is put under pressure before the implant is inserted. The pressurisation has two principal effects: (a) it improves the quality and strength of the bone cement material, and (b) it improves the strength of the interlock between the cement and the bone into which the cement is placed, since the cement is thus encouraged to penetrate into the interstices of the bone structure. Both these effects are desirable.

A number of devices are available which attempt to carry out such cement pressurisation. A typical device is that developed by the present inventors and shown in U.K. Pat. No. 1,430,083. This specification describes an inflatable seal, and its method of use is as follows. Firstly, the cavity in the bone into which the cement is to be placed is formed by the surgeon. The cavity should be open at one part only, and the medullary canal, for example, will need to be sealed at its distal end by a suitable plug before insertion of the cement. Such a plug is the subject of U.K. Patent Specification No. 2,054,383. Once the cavity in the bone is completed, bone cement is introduced into the cavity either by hand or by using a cement syringe or gun similar to that described in U.K. Patent Specification No. 1,603,102. After withdrawal of the syringe or gun, pressurisation may now take place by forming a seal over the bone cement, completely enclosing the opening of the bone cavity, using the inflatable pressuriser device of U.K. Pat. No. 1,430,083. The pressuriser is then forced manually down onto the surface of the cement, causing the total volume of the closed cavity to be descreased. The cement, being virtually incompressible, is put under pressure and forced to flow into the pores of the bone itself. (These bony pores are often the trabecula bone.) Thus, this procedure involves two steps: firstly the bone cavity is filled with cement, and secondly a pressuriser device is applied to decrease the total volume of the closed cavity.

SUMMARY OF THE INVENTION

The present invention seeks to provide a device enabling an improved procedure.

According to the present invention there is provided apparatus for use in pressurisation of cement in a cavity in a bone, comprising a seal member for fitting over and sealing the opening of the cavity, characterised in that the seal member has an aperture therethrough arranged to receive sealingly a nozzle for the delivery of cement. This facilitates a surgical procedure in which pressurisation of cement in the cavity is achieved not so much by a reduction in volume in the cavity, but rather by introduction of further cement through the aperture in the seal while the seal is held in sealing relationship over the opening of the cavity.

The apparatus may further include abutment means comprising a member adapted to overlie the seal member, the abutment member having an aperture therethrough arranged to receive said delivery nozzle, said abutment means being urgeable to urge said seal member to seal the bone cavity opening. Preferably said urging of the abutment means is effectable by a dispensing means such as a gun or syringe which provides said delivery nozzle.

Such abutment means may enable the seal member to be maintained sealingly against the bone cavity opening by force applied to the cement gun or syringe barrel without the need for an additional operator.

In further aspects the invention provides: abutment means; a cement gun (or syringe) assembly including such abutment means; and a cavity-filling assembly comprising such a gun/syringe assembly and a seal member. The seal member and the abutment means may be mutually adapted to each other and to the bone cavity opening (or to an expected range of types of bone cavity opening).

The seal may be a flexible, liquid-containing bag or ballon so as to facilitate achieving a sealing relationship over the irregular surface of the opening of bone cavity. The seal may be inflatable with the liquid, or it may be permanently filled with the liquid. More preferably the seal member comprises a substantially solid body. A suitable material is viscoelastic, conformable polymeric material. Of course, whatever form the seal member member takes, it must be (at least externally) of surgically acceptable material(s).

BRIEF DESCRIPTION OF THE DRAWINGS

Preferred embodiments of the invention will now be described in connection with two surgical procedures, with reference to the accompanying drawings, wherein.

DESCRIPTION OF THE PREFERRED EMBODIMENTS

Figure 1:
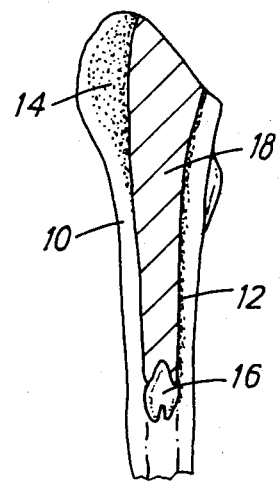
FIGS. 1 to 3 are diagrammatic cross-sections through the upper end of a human femur, showing successive stages of pressurisation of bone cement within a medullary cavity.

Referring to the first procedure for pressurising cement in a medullary cavity in a femur, FIG. 1 shows the upper end of a femur 10, the medullary canal 12 of which has been reamed out to receive the stem of an implant such as a prosthetic hip device. It will be appreciated that the cavity thus formed is lined by cancellous bone 14. A plug 16 is inserted to seal the distal end of the medullary cavity. This plug is suitably as described in our U.K. Specification No. 2054383. The cavity is then filled with polymethylmethacrylate bone cement 18, using the syringe or gun described in our British Pat. No. 1603102.

Figure 2:
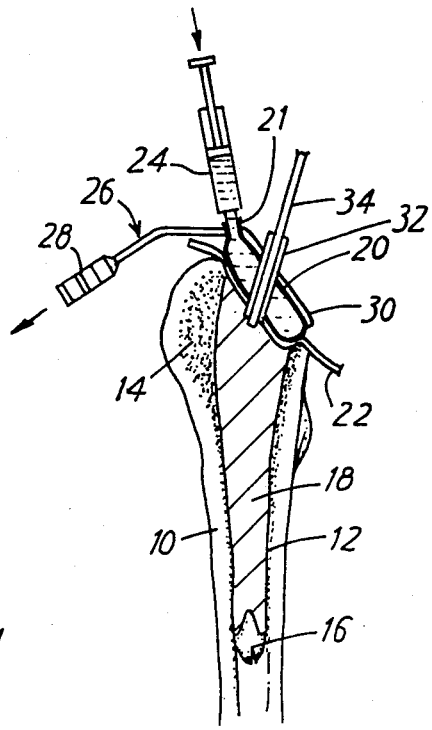

In order to increase the cement's strength and cause its intrusion into the pores of the cancellous bone, the cement 18 is now pressurised as follows. Referring to FIG. 2, a flexible ballon seal 20 is placed over the open end of the medullary cavity 12, with an intermediate rubber sheet 22. The purpose of the rubber sheet is to facilitate subsequent removal of the seal, since the rubber sheet will have less tendency to stick to the cement 18. The balloon 20 is made from an extensible material such as rubber, and is generally in the form of a flat cylinder. It is provided with an opening 21, and it is now filled with water or another medically inert liquid through this opening, by means of a syringe 24. This causes the seal 20 to inflate, and it can be pulled onto the bone around the opening of the medullary cavity by an assistant surgeon who pulls it down using an instrument 26. The instrument 26 has a pulling handle 28 and a flat plate 30 which bears on the seal 20, This gives a certain amount of pressure to the liquid inside the seal 20, causing it to seat firmly (through the rubber sheet 22) onto the bone all the way round the opening to the medullary cavity 12. It will also give a degree of pressurisation to the cement 18.

The balloon seal 20 is annular in form, having an aperture defined by a sleeve 32 passing through a central region thereof. This sleeve can be at an angle with respect to the seal, as shown in FIG. 2, in order to conform to the preferred direction of working. However, since the seal is flexible this is not too critical. The sleeve 32 receives the delivery nozzle 34 of the cement gun, and is flexible, so that when the seal 20 is inflated with liquid and pressure is applied to it by means of the instrument 26, a seal is also formed around the nozzle 34. The cement gun may be the same cement gun as used above. The rubber sheet 22 and the plate 30 of the instrument 26 are also provided with suitable central apertures to accommodate the nozzle 34.

Figure 3:
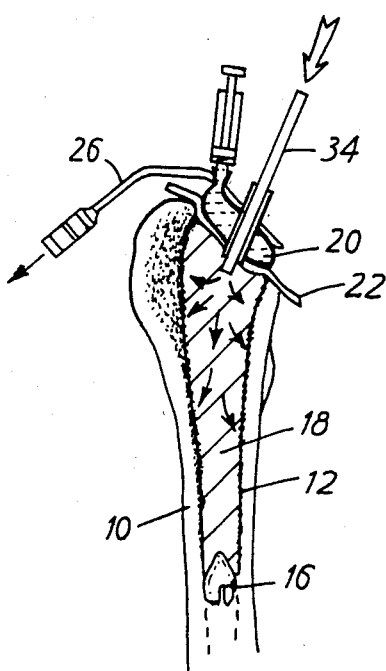

Now that the inflated seal 20 is forming a seal both around the cut bone around the top of the medullary cavity 12, and around the nozzle of the gun 34, further cement is injected into the cavity 12 as indicated by the arrows in FIG. 3. Because of the seal formed at the end of the medullary cavity 12, this causes pressurisation of the cement 18, causing further intrusion into the pores of the cancellous bone, and giving the necessary strength to the cement when it cures. The nozzle 34 of the cement gun, the instrument 26, the balloon seal 20 and the rubber sheet 22 can now be removed, the desired implant can be placed in the cement in the medullary canal, and the cement allowed to cure.

Figure 4:
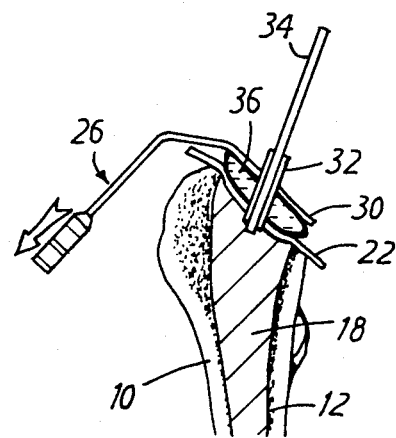
FIG. 4 is a view corresponding to FIG. 2 but showing a second embodiment of the invention.

FIG. 4 shows an alternative kind of seal 36. In place of the inflatable balloon seal 20, the seal 36 is a floppy, closed bag containing a fixed amount of a liquid such as water. Thus, instead of being made from an expandable rubber like material which is inflated by injecting liquid into it, the material from which the bag is made is not extensible. As before, the bag is flexible so that it can form itself over non-uniform shapes such as the cut bone at the open end of the medullary cavity 12, and it has the same general shape as before, but its total volume is constant. Its method of use is exactly the same as previously, and so will not be described further.

As a further alternative, the seal could be a substantially solid member of conformable polymer. This is at present preferred.

Figure 5:
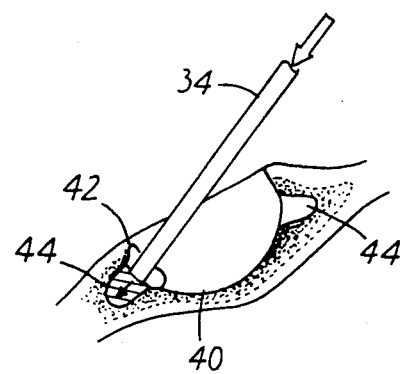
FIGS. 5 and 6 are diagrammatic cross-sections of a human acetabulum showing successive stages of pressurisation of bone cement in a cavity formed therein.
Figure 6:
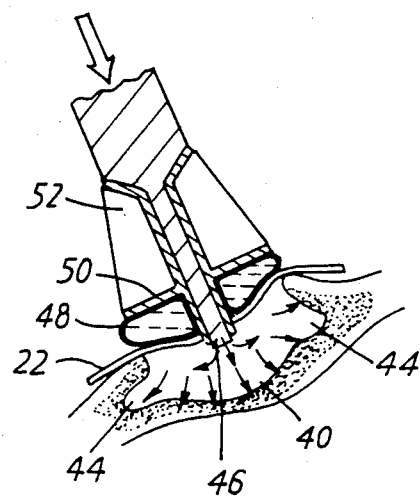

FIGS. 5 and 6 show a method of pressurizing cement in a cavity surgically formed in the human acetabulum. This is the other half of an operation to give a total replacement hip joint to a patient, since into such a cavity in the acetabulum is placed an artificial acetabular cup with which a ball on the implant placed in the femur co-operates to form a ball and socket joint.

The method uses the same principle as that described above, namely (a) the formation of a closed cavity in a bone by the surgeon, (b) the introduction of cement into the cavity, (c) closing the cavity with a sealing instrument, and (d) injecting more cement into the closed space.

In detail, the procedure is as follows. Referring to FIG. 5, the cavity 40 in the acetabulum is prepared together with three fixation pits 44 extending therefrom, in the illium, the ischium and in the pubic ramus. Each of these pits is cleaned and separately injected with bone cement from a cement gun through a nozzle 34 thereof, the end of which is fitted with a small annular seal 42. Some pressurisation to the cement in the fixation pits 44 is possible at this stage by forcing cement through the nozzle 34 while pressing down to hold the flexible seal 42 against the opening of the fixation pit. The main bolus of cement is now introduced into the cleaned acetabular cavity 40. Referring to FIG. 6, a rubber sheet 22 is now applied as previously over the end of the filled cavity, the sheet 22 having an opening in the central region thereof to accommodate a nozzle 46 of a cement gun. The nozzle 46 is fitted with an annular floppy bag seal 48 similar to that described in FIG. 4, and with a pressure flange 50 (of course one of the other types of seal could be used.) As seen in FIG. 6, the seal 48 is sandwiched between the pressure flange 50 and the rubber sheet over the opening of the cavity 40. The nozzle of the cement gun is also provided with an annular distance piece 52 of metal or plastics material, and this serves to transmit the manual pressure applied by the surgeon through the cement gun, onto the floppy bag seal 48 to cause it to give a good seal around the edges of the cavity 40. Cement is then injected by the cement gun through the nozzle 46, to pressurise the cement already in the cavity 40 and the fixation pits 44, causing intrusion of cement into the cancellous bone and giving strength in the cement when cured, as previously. The nozzle 46, the seal 48 and the rubber sheet 42 are now removed, and the prosthetic acetabular cup can be inserted in the cement in the usual manner.

FIGS. 7 to 10 deal with a slightly modified procedure which does away with the need for a separate pressurising instrument 26 to be operated by an assistant. It is shown in its application to pressurising cement into the medullary canal of a femur 10. The opening of the canal 12 is elongate, and so the seal member 114 is elongate and, sausage-shaped. The illustrated seal member is a balloon seal, i.e. a liquid-containing flexible bag, with means 116 for charging or discharging liquid. It has a central aperture defined by a sleeve 118 for receiving sealingly the nozzle 34 of a cement gun. (It is generally as described above in connection with FIGS. 1 to 3.)

Figure 7:
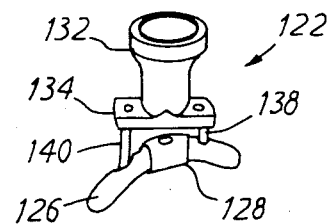
FIG. 7 is a perspective view of abutment means for use in a further embodiment of the invention.
Figure 8:
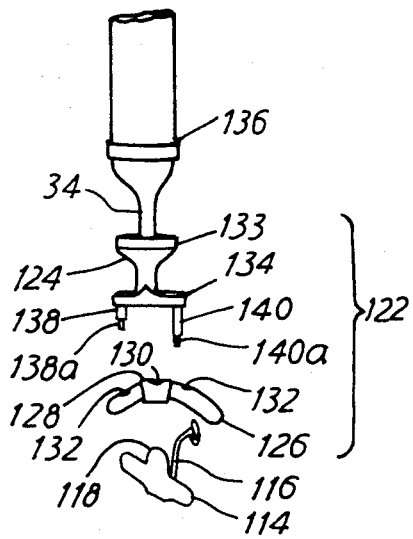
FIGS. 8 and 9 show a filling assembly including the abutment means shown in FIG. 7, FIG. 2 being an exploded view and FIG. 3 showing the parts assembled for use.
Figure 9:
Figure 9:
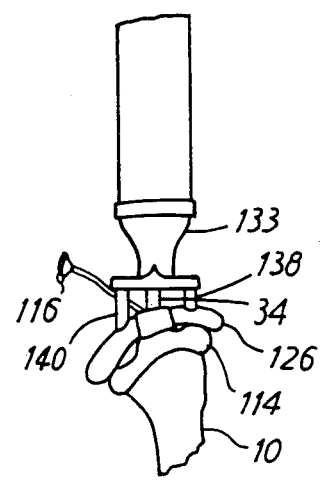

An abutment means 122 of FIGS. 7 to 9 consists of a distance piece 124 and an abutment member or pressure piece 126. The pressure piece 126 has an asymmetrical banana shape. It is generally of constant round cross-section. In this embodiment there is a wider, collar portion 128 at an intermediate region. This is penetrated by an aperture 130 for receiving the nozzle 34. Each of the two arms of the banana shape has a blind bore 132 facing upward and parallel with the aperture 130.

The distance piece 124 has an upper funnel portion 133 and a lower bridge portion 134. The funnel portion fits over the end of the barrel 136 of a cement gun. The nozzle 34 passes through the funnel portion 132 and through an aperture in the bridge portion 134. The bridge portion 134 is laterally elongate, and has a downwardly extending leg 138, 140 at each side portion. The two legs are of unequal length. Each has a lower portion 138a, 140a of reduced diameter, adapted to be received snugly in a respective blind bore 132 in the pressure piece.

In use, as shown in FIG. 9 the cement gun is pressed with its barrel end 136 abutting within the funnel portion 132 of the distance piece. The thrust is transmitted, via the legs 138, 140 engaging in the bores 132, to the pressure piece 126. This is shaped so as to urge the seal member 114 against the canal opening 12. (Note how the combination of the unequal legs 138, 140 and the unsymmetrical banana shape of the pressure piece matches the member 114 to the canal opening 12.) The nozzle 34 of the cement gun extends into the medullary cavity, so that cement can be pumped in.

If the illustrated type of fillable seal member 114 is used, it is filled with liquid (e.g. sterilised water) before the cement is pressurised, as described above with reference to FIGS. 1 to 3. If on the other hand a solid seal is used, it is forced down onto the femur by the pressure piece 126, and deforms to the shape of the bone. (Its intrinsic shape may be subtantially identical to that of the member 114 as seen in FIG. 8.)

The person skilled in the art will be able to select a suitable material for making a solid seal on the basis of the information already given. By way of example, we would mention the plastics materials known by the trade names of Sorbothane and Sarathon, both produced by Professor M. Hiles, University of Akron, U.S.A. The former has been suggested for lining shoes, to take shock loads, but the latter is perhaps preferable for present purposes. A solid seal (with an aperture defined by a sleeve 118) can be made in such a material. It may be re-usable, but on grounds of hygiene it is preferable to use a new seal for each operation. This is of course much more practicable (in terms of cost) than when using a balloon seal.

Both materials are viscoelastically conformable. That is, they are resiliently deformable rather like rubber, but the deformation properties vary with the nature of the deforming force.

Figure 10:
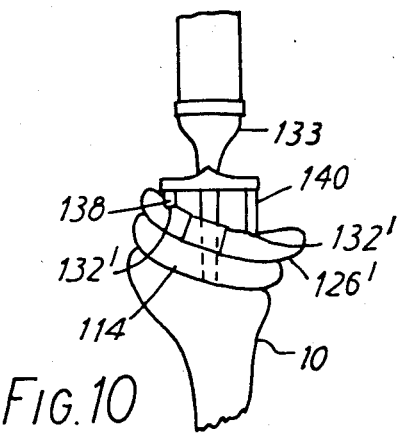
FIGS. 10 and 11 are similar to FIG. 9 but showing further forms of abutment means.

It may be convenient to use the pressure piece either as shown in FIGS. 7 to 9, or the other way round as shown in FIG. 10. The apparatus shown here differs only in that the pressure piece 126' has through-holes 132' and not blind bores. These holes 132' serve to seat the legs 138, 140 in either orientation of the pressure piece 126'.

Figure 11:
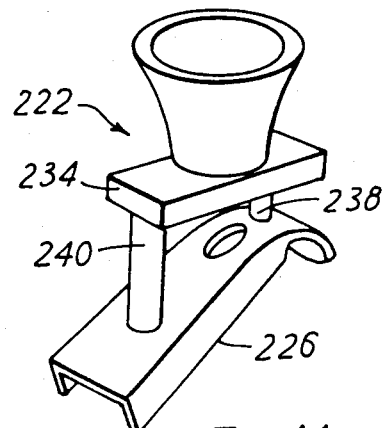

FIG. 11 shows a modified abutment means 222, which differs from that of FIGS. 7 to 9 primarily in the form of the pressure piece 226. This is a shaped piece of sheet metal, rigidly attached to the legs 238, 240 of the bridge portion 234. It has a substantially straight channel-section portion, and a downwardly curving portion at one side. It is for use with a femoral seal of solid conformable polymer.

The preceding description and FIGS. 7 to 10 refer to the medullary canal of a femur. Of course the apparatus is applicable to many other situations, e.g. in filling an acetabular cavity. Different types of cavity may call for differently shaped seal members 114, and these in turn may call for differently shaped pressure pieces 126.

For example, in filling an acetabular cavity we may use a thick disc or doughnut-shaped seal member 114 made of a solid viscoelastic conformable material as described above. An appropriately configured pressure piece will be used.

Even when considering a single type of bone, e.g. the femur, there is considerable variation in form. It may be possibe to produce a pressure piece whose curvature and form make it usable with (e.g.) virtually all human femurs. Alternatively, the availability of a range of pressure pieces, and/or the reversibility described with reference to FIG. 10, may be desirable.

While the invention has been illustrated above with reference to the preferred embodiments, it will be understood by those skilled in the art that various changes may be made without departing from the spirit and scope of the invention, and it is intended to cover all such changes and modifications by the appended claims.

We claim:

1. Apparatus for use in pressurization of cement in a cavity in a bone, said apparatus comprising a seal member for fitting over and sealing the opening of the cavity, said seal member being deformable and having an upper and lower substantially planar surfaces and further including a transverse aperture for sealingly receiving a cement delivery nozzle extending through a central region thereof, said seal member being dimensioned and arranged so as to be urgeable transversely, with a said nozzle extending through said aperture in sealing relationship with the portions of said seal member defining the aperture, with deformation of the seal member, said lower planar surface disposed in substantially coplanar relationship with the surfaces of the bone defining the opening of the cavity so as not to invade the cavity and to extend beyond the edges the opening of the cavity to contact the surfaces of the bone defining the cavity to provide sealing around the cavity, said seal member further providing sealing directly around the delivery nozzle, whereby cement under pressure can be passed through the nozzle into the sealed cavity and provide complete filling of the cavity.

2. Apparatus according to claim 1 wherein the seal member comprises a flexible, liquid-containing bag deformable to facilitate sealing at an irregularly-shaped cavity opening.

3. Apparatus according to claim 2 wherein the bag has means for inflation with liquid.

4. Apparatus according to claim 3 wherein the bag is resiliently extendible by inflation.

5. Apparatus according to claim 1 wherein the seal member comprises a substantially solid body.

6. Apparatus according to claim 1 further including abutment means adapted to overlie the seal member and having an aperture therethrough arranged to receive said delivery nozzle; said abutment means having means for urging it to urge said seal member against said bone cavity opening.

7. Apparatus according to claim 6 wherein in use, said delivery nozzle is provided by a dispensing means and wherein said urging means is an abutment surface of the abutment means arranged to be abuttable against by a said dispensing means.

8. Apparatus according to claim 7 wherein said abutment means comprises an apertured pressure piece shaped to urge the seal member against the cavity opening.

9. Apparatus according to claim 8 wherein said pressure piece is substantially banana-shaped.

10. Apparatus according to claim 8 wherein the abutment surface is provided by an abutment assembly comprising an apertured bridge piece arranged to contact the pressure piece on either side of its aperture, and a receiving portion adapted to receive an end portion of said dispensing means.

11. Apparatus according to claim 5 wherein said substantially solid body is of a viscoelastically conformable material.

12. A method of pressurizing cement in a cavity in a bone in a surgical procedure, said method comprising the steps of:

placing a seal member over the bone around the open end of the cavity in substantially co-planar relationship with the surfaces of the bone defining the cavity opening so as not to invade the cavity, said seal member having an aperture therethrough and being of a size such that the seal member extends beyond the edges of cavity and contacts the surfaces of the bone defining the cavity;

causing a cement delivering nozzle to extend sealingly through said aperture; and passing cement through said nozzle into the cavity while urging said seal member to seal said cavity, so as to completely fill said cavity including the uppermost portion of the cavity adjacent to the cavity opening.

* * * * *